United States Patent
Forget et al.

(10) Patent No.: US 9,351,987 B2
(45) Date of Patent: May 31, 2016

(54) COMPOSITIONS FOR TREATING HEARTWORM INFESTATION

(75) Inventors: Patrick Forget, Merignac (FR); Vassilios Kaltsatos, Libourne (FR); Stephan Warin, Libourne (FR)

(73) Assignee: CEVA SANTE ANIMALE, Libourne (FR)

( * ) Notice: Subject to any disclaimer, the term of this patent is extended or adjusted under 35 U.S.C. 154(b) by 0 days.

(21) Appl. No.: 13/813,276

(22) PCT Filed: Jul. 29, 2011

(86) PCT No.: PCT/EP2011/063129
§ 371 (c)(1),
(2), (4) Date: Mar. 25, 2013

(87) PCT Pub. No.: WO2012/013791
PCT Pub. Date: Feb. 2, 2012

(65) Prior Publication Data
US 2013/0172281 A1    Jul. 4, 2013

Related U.S. Application Data

(60) Provisional application No. 61/369,472, filed on Jul. 30, 2010.

(51) Int. Cl.
*A61K 31/7048* (2006.01)
*A61K 9/00* (2006.01)
*A61K 45/06* (2006.01)

(52) U.S. Cl.
CPC ........... *A61K 31/7048* (2013.01); *A61K 9/0024* (2013.01); *A61K 45/06* (2013.01)

(58) Field of Classification Search
CPC .................................................. A61K 31/7048
USPC ........................................................... 514/29
See application file for complete search history.

(56) References Cited

U.S. PATENT DOCUMENTS 5,728,719 A    3/1998    Miller

FOREIGN PATENT DOCUMENTS

| EP | 0473223 | 3/1992 |
|---|---|---|
| WO | WO 03/002102 | 1/2003 |
| WO | WO 2012/013782 | 2/2012 |

OTHER PUBLICATIONS

Cunningham, C.P. et al. "Evaluation of a covered-rod silicone implant containing ivermectin for long-term prevention of heartworm infection in dogs" *American Journal of Veterinary Research*, Sep. 2006, pp. 1564-1569, vol. 67, No. 9.

*Primary Examiner* — Leigh C Maier
(74) *Attorney, Agent, or Firm* — Saliwanchik, Lloyd & Eisenschenk

(57) ABSTRACT

The present invention further relates to ivermectin, most preferably formulated as an implant for administration of pet and domestic animals. These formulations provide long term protection against *Dirofilaria* parasites, without the risks for secondary adverse events of conventional formulations. Preferred formulations are implants and are administered at least twice a year, once a year, or at least once in 18 months, up to 24 months.

1 Claim, No Drawings

COMPOSITIONS FOR TREATING HEARTWORM INFESTATION

CROSS-REFERENCE TO RELATED APPLICATIONS

This application is the U.S. national stage application of International Patent Application No. PCT/EP2011/063129, filed Jul. 29, 2011, which claims the benefit of U.S. Provisional Patent Application No. 61/369,472, filed Jul. 30, 2010, the disclosures of which are hereby incorporated by reference in their entireties, including all figures, tables and amino acid or nucleic acid sequences.

FIELD OF THE INVENTION

This invention relates an improved antiparasitic composition for controlling heartworm infestation in an animal subject. The current invention also provides novel routes and regimens of administration.

BACKGROUND

Heartworm is a parasitic roundworm (especially *Dirofilaria immitis* and *Dirofilaria repens*) that is spread from host to host through the bites of mosquitoes. The definitive host is the dog but it can also infect cats, wolves, coyotes, foxes and other animals, such as ferrets, sea lions and even bovines and humans. The parasite is commonly called "heartworm" because the adult reproductive stage of its life cycle resides primarily in the right ventricle of its host where it can live for many years. Heartworm infection may result in serious disease for the host. When a mosquito bites an infected animal, young heartworms called microfilariae enter into that mosquito's system. Within two weeks, the microfilariae develop into infective larvae inside mosquitoes; these infective larvae can be transmitted to another animal when mosquitoes take their next blood meals. Upon entering the dog's circulatory system, the larvae develop and migrate to the dog's heart where they mature and breed. *Dirofilaria* young, termed "microfilariae," migrate throughout the hosts' circulatory system, where they may be ingested by a mosquito that feeds upon the infected hosts. The *Dirofilaria* life cycle is completed when the ingested microfilariae mature into infective larvae in the mosquito. Development of the larvae into adult worms takes about 180 days in dogs.

*Dirofilaria immitis* presents as white threadlike round worms reaching up to 20 cm for adult males (12-20 cm) and 31 cm for adult females (25-31 cm), with a mean diameter of 1 mm. They are characterised by a relatively smooth cuticle. Heartworms are primarily found in the pulmonary artery in dogs with low parasitic burden (<50 worms). In infestations with high parasitic burden (>50 worms), they may reach the right ventricle, right atrium, and occasionally vena cava. The initial response includes swelling of small pulmonary arteries and blood clotting. The physical presence of the heartworm parasite in the pulmonary artery and right ventricle of the canine heart, and the resulting destruction of tissue, causes respiratory and circulatory problems which can be fatal under conditions of stress or vigorous exercise. Pulmonary hypertension and right-sided congestive heart failure may result. Because it takes a large number of heartworms to clog up blood flow to a significant degree, heartworms can be present inside the heart for up to 2 or 3 years before causing clinical signs. As the disease progresses, lung tissue can be destroyed leading to a worsening cough and liver and kidney damage can occur due to reduced blood flow to these organs. If left untreated, heartworm disease may result in death. After adult heartworms mate and produce immature heartworms, an infected dog which is bitten by an uninfected mosquito will transmit microfilariae to the mosquito, beginning the cycle again. The life cycle of the heartworm is approximately 6 months. The heartworm parasite has also been shown to be the cause of focal lung, liver, eye and cutaneous lesions in man (Hamilton, R. G., et al., Exper. Parasitol., 56:298-313 (1983)).

Heartworm disease due to *Dirofilaria immitis* and/or *Dirofilaria repens* continues to cause severe disease and even death in dogs and other animals (cats, bovines, humans, guinea porcine, and ferrets) in many parts of the world, even though safe, highly effective and convenient preventatives have been available for the past two decades. Moreover, the parasite and vector mosquitoes continue to spread into areas where they have not been reported previously. The control of such parasites has long been recognized as an important aspect of human and animal health regimens. Although a number of alternatives to control infestation are in use, these suffer from a variety of problems, including a limited spectrum of activity, the need for repeated treatment (lack of compliance) and, in some rare instances, resistance by parasites.

Currently for curative treatment, only two arsenic derivatives are available for clinically infested dogs, namely thiacetarsamide (Caparsolate® marketed by Abbott laboratories) which is an old medication, with severe adverse effects and melarsomine dihydrochloride (Immiticide® marketed by Merial), which is a more recent drug with fewer side effects.

For chemoprophylaxis, two alternatives are possible to prevent heartworm disease in dogs: daily administration of diethylcarbamazine citrate, or monthly administration of macrocyclic lactones.

Number of macrocyclic lactones have commercialized, for example ivermectin under the name of Ivomec® or Heartgard® marketed by Merial, doramectin (Dectomax®, marketed by Pfizer Animal Health), moxidectin and abamectin (Avomec®, marketed by Merial).

Also, a slow release formulation of subcutaneously injected moxidectin-impregnated lipid microspheres, providing single dose continuous protection in excess of six months, has been marketed by Fort Dodge under the name of Moxidectin SR®, ProHeart 6® or Guardian SR®. However, this product was voluntarily removed from the US market in September 2004 for issues related to safety, and currently has been allowed once again by FDA under a risk minimization and restricted distribution program.

Ivermectin consists of a mixture of two homologous compounds, 22, 23-dihydroavermectin B1a (H2B1a, not less than 80%) and 22, 23-dihydroavermectin B1b (H2B1b, not more than 20%) as described in U.S. Pat. No. 4,199,569. The invention relates to use of said mixture.

Ivermectin has been marketed for treatment of various helminth intestinal parasites including heartworm in animals. Currently approved Heartgard® chewable tablets are administered orally at monthly intervals at the recommended minimum dose level of 6.0 mcg of ivermectin per kilogram (2.72 mcg/lb) of body weight. Heartgard® is available in three dosage strengths for dogs of different weights (68, 136 and 272 mcgs). For other species like swine, cattle, sheep, and horses, ivermectin is available in 10 mg/ml and 2.7 mg/ml injectable form; 0.153 percent and 1.87 percent paste form; 10 mg/ml liquid oral form.

High plasma total ivermectin concentrations are however considered a risk factor for diseases of the nervous systems in dogs. In a 36-clay study in beagle dogs in which ivermectin was administered orally at 0.5 and 2.0 mg/kg of body weight (bw), the concentrations of H2B1a in plasma increased dramatically between days two and eight and reached steady-state after about three weeks. A four-fold increase in the dose resulted in an average eight-fold increase in plasma levels. Such high plasma levels have been observed to cause adverse effects in dogs. In beagle dogs, mydriasis was the most sensitive indicator of toxicity. More severe signs included ataxia and tremors. Deaths were preceded by a comatose state. Approximately 30% of collie dogs were highly sensitive to ivermectin (as estimated from reports from non recommended use of the drug). In a 14-week oral study in beagle dogs (4/sex/group), mydriasis and slight weight loss were observed at 1.0 and 2.0 mg/kg bw. Four dogs in the 2.0 mg/kg bw group developed tremors, ataxia, anorexia and dehydration and were killed prior to the end of the study. The No Observable Effect Levels (NOEL) was 0.5 mg/kg bw. It is now reported that collies are the most frequently affected dogs.

It is known, in humans and in several animal species, that altered expression or function of p-glycoprotein could conceivably allow elevation of brain concentrations of ivermectin and produce severe neurotoxicity. As a consequence of normal dosing regimen for ivermectin, the treated animals necessarily receive a relatively large quantity of the drug which is to remain effective for an extended period. This in turn means that shortly after treatment the animal has a very high concentration of ivermectin in its bloodstream, with this concentration tailing off during the remainder of the period.

Further the currently marketed ivermectin formulations come with certain precautions for usage. The American Heartworm Society (AHS) recognizes the safety-net (or reach-back effect) and adulticidal properties of some macrocyclic lactones, particularly ivermectin. However, heartworm-positive working dogs might be more at risk to develop severe thromboembolism and death. Worsened radiographic and echocardiographic images with greatly restricted exercise suggest that such treatment is contraindicated. Furthermore, even in asymptomatic dogs, it should be administered only with much caution and with examination by a veterinarian at least once every 4-6 months. Likewise, ivermectin must be used with caution in collies and related shepherd dogs that are more susceptible to its neurotoxic effects than other dog breeds.

Accordingly, in order to overcome the foregoing problems, increase the effectiveness of avermectin in eradication of heartworms, and provide for more predictable performance of this drug, there is a need in the art for a dosage form which affords improved absorption and bioavailability of avermectin and more precisely of ivermectin at a lower maximum plasma concentration.

Further the present invention aims to provide novel formulations that are easier to administer and are able to maintain the effective plasma concentration over a prolonged period of time of at least 6 months, 12 months, or at least 18 months to 24 months. Generally topical applications are desirable since many formulations are acceptably safe when used topically, but not when used internally. However, developments of various topical pharmaceutical formulations have posed a number of drawbacks. Some formulations require a large volume to be applied to the animal. This can cause considerable mess and can lead to an unpleasant smell. Additionally, if the dosage of a topical formulation is in a large volume, it can be easily shaken off by the animal, thereby reducing the effectiveness of the formulation. Also, when the animal is a house pet, there is a further complication in that the formulation should be safe for human contact. It should also not lead to staining of furniture, carpeting and the like. Finally, even if safe, topical formulations should not be irritating or lead to rashes, hair loss or exhibit other unpleasant side effects.

SUMMARY OF THE INVENTION

There is therefore a need for an improved formulations for the treatment of endoparasites and ectoparasites that overcome drawbacks of the prior art. The present invention provides herein such improved formulations, especially as implants that are capable of delivering ivermectin alone or in association with at least one ectoparasitic or endoparasitic control agent, thereby providing long term efficient activity against endo- and/or ectoparasites for at least 6 months to 18 months and up to around 24 months.

The present invention further relates to ivermectin, most preferably formulated as an implant for administration of pet and domestic animals. These improved formulations achieve effective plasma levels faster and at lower concentrations of the drug, are stable on storage, and exhibit good tolerability characteristics. Also, these formulations provide long term protection against parasites, for at least 6 months, at least 12 months or 1.8 months and up to 24 months without the risks for secondary adverse effects of conventional formulations. Preferred formulations are implants and are administered at least twice a year, once a year, once two year and most preferably at least once in 18 months.

The present invention provides an improved method of controlling heartworm infestation such as for example dirofilariosis, by administering an effective dose of an avermectin sufficient to achieve a reduction in *Dirofilaria immitis* and/or *Dirofilaria repens* in a subject, at a lower plasma concentration of avermectin as compared to plasma avermectin concentration obtained via conventional avermectin formulations.

The invention also provides a method of controlling heartworm infestation, comprising administering to a non-human animal subject a composition comprising an effective dose of ivermectin to control *Dirofilaria immitis* and/or *Dirofilaria repens* infestation, wherein said ivermectin composition is in the form of an implant, and said composition is administered at least twice a year, once a year, once in 18 months, or once in 24 months.

The present invention further provides avermectin formulations having significant parasiticidal activity for controlling heartworm infestation, at a lower plasma concentration as compared to the conventional avermectin formulations. These formulations are safe to use and avoid the many common deleterious side effects of conventional formulations.

The present invention also provides implants that comprise an effective dose of an avermectin which can be effective to control heartworms infestation, at a lower plasma concentration as compared to the conventional avermectin formulations. The compositions derived herein can also be useful to improve the speed of result and decrease the reoccurrence, compared to other formulations. Preferably the implant comprises an effective dose of ivermectin.

The formulations according to the present invention are in the form of implants which may be administered at least twice a year, once a year, at least once in 18 months or in 24 months.

The present invention still further provides an antiparasitic combination comprising an effective dose of an avermectin, such as ivermectin, for treating and/or preventing and/or controlling *Dirofilaria immitis* and/or *Dirofilaria repens* alone or in association or in combination with at least one ectoparasitic or endoparasitic (control) agent.

DETAILED DESCRIPTION

Definitions

As used herein avermectins refer to the most potent anthelmintic, insecticidal and acaricidal compounds known. Several avermectins have been developed, including, ivermectin, abamectin, doramectin, eprinomectin and selamectin. Ivermectin is preferably used in intradermic and/or subcutaneous compositions, such as implants and methods according to the present invention.

"Conventional avermectin formulations" refers to Heartgard® chewable tablets marketed by Merial, Heartgard® 10 mg/ml and 2.7 mg/ml injectable form; 0.153 percent and 1.87 percent paste form and 10 mg/ml liquid oral form.

"Subject" or "animal subject" refers to any non human animals able to develop pathologies related to heartworms such as, for example, pet animals. Canines may be the preferred subjects of the present invention. The subject is typically a non-human mammal, and may be any such animal mentioned herein.

"Heartworms" generally may include roundworms that typically reside within the heart of a host during the final reproductive stages of its life cycle. Some specific heartworms may include *Dirofilaria immitis* and *Diroflaria repens* and any other similar worms of the same class or subclass.

"Combination" as used herein may broadly include two or more elements or compounds physically, chemically, and/or otherwise suitably coupled with each other to produce a desired result. Both components of the combination may be administered simultaneously or sequentially and may be separate dosage forms or may be part of same dosage form.

"Controlling" as used herein may broadly include the reduction, the treatment, the eradication and/or the prevention of *Dirofilaria immitis* and *Dirofilaria repens* and any other similar worms of the same class or subclass.

The present invention thus aims at developing improved formulations of an avermectin, particularly ivermectin, that overcome the disadvantages and constrains of existing treatment and provides a method of controlling infestation and a dosage form that can be easily and safely administered to produce an efficacious response across many species susceptible to heartworm infestation/infection.

Currently approved dosages of ivermectin are about 6 mcg/kg orally or 200 mcg/kg subcutaneously. It is generally reported that ivermectin administered per se at 6 mcg/kg is able to kill efficiency one month aged *Dirofilaria larvae*. Cunningham C P et al., (Am. J. Vet, Res., 2006, 67) brought evidence that this effective rate might be around 0.2 ng/mL of ivermectin in the plasma.

The background art does not teach or suggest a method or formulation of ivermectin, providing a lower effective concentration of the active ivermectin drug relative to that resulting from the administration of conventional ivermectin formulations, whilst maintaining the efficacy and exhibiting improved safety profile. The present inventors have surprisingly established an effective rate at around 0.1 ng/mL of ivermectin in the plasma. Also, the formulations according to the present invention provide a long term protection, e.g., at least 6 months, 12 months, or 18 months up to 24 months against infections caused by parasites.

Accordingly in a preferred embodiment, the current invention provides a method of controlling heartworm infestation by administering an effective dose of ivermectin which achieves a reduction in *Dirofilaria immitis* and/or *Dirofilaria repens* in a subject, at a lower plasma concentration of ivermectin as compared to plasma ivermectin concentration obtained via conventional ivermectin formulations as defined by Cunningham C P et al. (Am. J. Vet. Res., 2006, 67). In a preferred embodiment, said lower plasma ivermectin concentration is less than 0.2 ng/mL, or less to 0.15 ng/mL, ranges from 0.1 ng/mL to 0.15 ng/mL, around 0.09 ng/mL, 0.08 ng/mL, 0.07 ng/mL, 0.06 ng/mL, or about of 0.1 ng/mL. In a most preferred embodiment the said lower plasma ivermectin concentration is about 5-95% of conventional ivermectin formulations, particularly preferred plasma concentration is about 50% of conventional ivermectin formulations.

In another preferred embodiment, the present invention provides a composition for controlling heartworm infestation in a subject or the use of a composition for controlling heartworm infestation, wherein the composition is effective at a lower plasma concentration of ivermectin as compared to conventional ivermectin formulations, and exhibits a reduced side effect profile as compared to a conventional formulation. In a preferred embodiment, said lower plasma ivermectin concentration is less than 0.2 ng/mL, or less to 0.15 ng/mL, ranges from 0.1 ng/mL to 0.15 ng/mL, around 0.09 ng/mL, 0.08 ng/mL, 0.07 ng/mL, 0.06 ng/mL, or is about of 0.1 ng/mL. In a most preferred embodiment the said lower plasma ivermectin concentration is about 5-95% of conventional ivermectin formulations, particularly preferred plasma concentration is about 50% of conventional ivermectin formulations.

The present invention also provides novel active composition for controlling or eradicating *Dirofilaria immitis* and/or *Dirofilaria repens* infestation in subject, comprising a combination of an avermectin, preferably ivermectin and at least one other ectoparasitic or endoparasitic (control) agents. Said composition may be administered and used in the manner described herein for other compositions, including the dosage, time period or (implanted) form.

The formulations of the present invention are preferably administered for intradermic and/or subcutaneous application via shaped articles. Most preferably shaped articles are implants.

When compared to the existing treatment options, e.g., chewables, spots on which are administered monthly, injectable suspensions which a long term action, i.e., 6-12 months, the implant formulation does not contain any aggressive solvent (contrary to the spot on product), has a long duration of action. Preferably, the implant formulation according to the present invention, comprises a therapeutically effective amount of ivermectin having a systemic action and/or an agent active against internal parasites and are administered to the animals at least once in 6 months, 12 months, or once in 18 months up to once every two years.

The compositions of the present invention may be in the form of implants comprising an amount of ivermectin sufficient to achieve a plasma concentration of less than 0.2 ng/mL, or less to 0.15 ng/mL, ranges from 0.1 mg/mL to 0.15 ng/mL, around 0.09 ng/mL, 0.08 ng/mL, 0.07 ng/mL, 0.06 ng/mL, or is about of 0.1 ng/mL for a period of at least 6 months, 12 months, or at least 18 months and up to 24 months.

Implant formulation according to the present invention may be in the form of rods which have been extruded. Alternatively, the implant may be formulated in a dispersed matrix structure. Rod-like shape is preferred. Such rod-like shape may be circular cylinders, prisms, and elliptical cylinders. When the implant is administered using an injector-type instrument, a circular cylinder device is preferred. Such implant may be solid or hollow devices, may have various dimensions of a few mm², and thus have a cross-sectional diameter of for example 0.2 mm to 4 mm, an axial length of about 0.2 to 30 mm, preferably 0.5 to 15 mm, and more preferably about 1 to 10 mm.

The rod-shape implant may have various lengths and sizes for implantation in the animal subject, and may comprise a sufficient amount of ivermectin so as to achieve an ivermectin plasma concentration as described above for a period of at least 6 months, 12 months, or 18 months and up to 24 months. More than one rod can be implanted in each animal. Also, they may be designed to provide extended or sustained or controlled release of an avermectin, preferably ivermectin, and effective at half the plasma concentration of conventional avermectin formulations for a period of at least 6 months, 12 months, or 18 months and up to 24 months.

The matrix formulated implant may be injected or otherwise surgically implanted into the body, where it remains as a depot from which the compound slowly dissolves, or is released by diffusion. Matrix formulations may comprise waxy semi-solids such as vegetable waxes and high molecular weight polyethylene glycols. Very effective sustained action is obtained by introducing into the animal subject an implant containing the effective amount of ivermectin.

Such implants are now well known in the veterinary art and may be formed from a biocompatible or a biodegradable material. The biocompatible material may be polyesters, polyamine acids, silicones, cellulose, ethylene-vinyl acetate copolymers, polyvinylalcohols, and silicone material. Such silicone material may be a porous silicon or biosilicon material. Preferred implants are made of a silicon rubber or other polymerized plastic such as methacrylate. Biodegradable material may be formed of water-soluble material. The water-soluble material may be for example synthetic polymers such as polyethylene glycol, polyethylene propylene glycol, or sugars, polysaccharides such as dextran, amino acids, mineral salts, organic salts, or proteins (gelatin and collagen).

Implants according to the present invention may include additional carriers or excipients, lubricants, fillers, plasticizers, binding agent, pigments, and stabilizing agents. Suitable fillers may be for example talc, titanium dioxide, starch, kaolin, cellulose (microcrystalline or powdered) and/or a mixture thereof. Binding agents may include polyvinyl pyrrolidine, hydroxypropyl cellulose and hydroxypropyl methyl cellulose and mixtures thereof.

The active ingredient is dispersed through the solid implant or is contained inside a hollow implant. The active ingredient is dispersed by first dissolving or mixing with the polymer, or dissolved in, or mixed with a carrier, it is dispersed within the polymer. After implantation, the active ingredient diffuses or leaches out of the solid or hollow implant into the body fluids of the treated animal. The rate at which the ivermectin is released from an implant, and hence, the length of time during which the implant remains effective, is controlled with good accuracy by the proper adjustment of the concentration of ivermectin in the implant, the external area of and amount of carrier in the implant, the external area of the implant, the formulation of the polymer from which the implant is made, the thickness of the wall of hollow implants and the diffusion characteristics of the ivermectin through the wall of the implant or through specially designed end-plugs of polymer or other membrane forming one or more surfaces of the implant, or by being forced through a porous membrane or aperture by an osmotic pump activated by absorption of body water into an osmotically active component contained in a second compartment of a hollow implant.

Administration of ivermectin by means of an implant is a further particularly preferred embodiment. Such administration is highly economical and efficacious because a properly designed implant maintains a constant concentration of the compound in the tissues of the host animal, and is easily inserted in the animal. No further handling of the animal or concern over the dosage is necessary after implant insertion. Said implant may be erodible/soluble or biodegradable and thus may be left in the animal tissue, or it may be insoluble/non-erodible and suitable for surgical removal after exhaustion of ivermectin.

The above dosage forms may be administered at a single time (e.g., as one dose) or at separate time points (e.g. divided doses). According to the present invention, the formulation may be administered as implant dosage form at separate time points, the interval between the separate administrations being at least 6 months, 12 months, preferably every 18 months up to every 24 months. Indeed, administration of ivermectin implant provides a long term protection against parasites for a period of at least 6 months, 12 months, at least 18 months to at least 24 months.

In an additional, preferred embodiment, the compounds in these amounts may be combined with other ectoparasitic or endoparasitic control agents.

In a particularly preferred embodiment, the present invention provides a kit useful in the control (treatment and/or prophylaxis) of heartworm infestation in a subject, which comprises a dose of ivermectin which achieves a reduction in or control of infestation of *Dirofilaria immitis* and/or *Dirofilaria repens* in subjects, at a lower plasma concentration of ivermectin as compared to plasma ivermectin concentration obtained via conventional ivermectin formulation, optionally in combination with ectoparasitic (ticks, fleas . . . ) or endoparasitic (*Ascaris, Ancylostoma* . . . ) agents, optionally a carrier, and instructions for the treatment or control of a parasitic infestation.

EXAMPLES

Example 1

Preparation of Implants Containing Ivermectin

The following ivermectin implant containing invermectin as listed in the following Table 1 was prepared.

TABLE 1

| ivermectine implant name | 3% | 4.5% | 6% |
| Ingredients | | Proportions % | |
| --- | --- | --- | --- |
| Ivermectin (%) | 15 | 22.5 | 30 |
| Ca Hydrogen Phosphate | 25 | 22.5 | 20.7 |
| Ethyl cellulose N50 | 42 | 38.5 | 38.5 |
| Sucrose | 10 | 9 | 1.5 |
| Ethyl cellulose N50 | 4 | 6 | 6 |
| Lubritab | 3 | 3 | 3 |
| Aerosil 200 | — | 0.3 | 0.3 |
| Total | 100 | 100 | 100 |

For the tests, 2 adult dogs have received the 6% ivermectin implant (dogs A and B), 1 adult dog have received the 4.5% ivermectin implant (dog C), and 1 adult dogs have received the 3% ivermectin implant (dog D).

The concentrations of ivermectin (ng/mL) in the plasma, collected in the jugular vein at day 0 to day 429, are presented in Table 2.

TABLE 2

| Days | Ivermectin ng/ml | | | |
|---|---|---|---|---|
| | Dog A | Dog B | Dog C | Dog D |
| 1 | 6.25 | 3.50 | 6.93 | 7.63 |
| 2 | 5.29 | 3.04 | 6.42 | 6.95 |
| 4 | 5.25 | 2.62 | 4.77 | 4.35 |
| 10 | 2.56 | 0.97 | 2.64 | 3.82 |
| 21 | 1.35 | 1.92 | 2.14 | 1.23 |
| 30 | 0.91 | 1.01 | 1.79 | 1.54 |
| 39 | 1.09 | 1.02 | 1.74 | 1.15 |
| 60 | 0.76 | 0.51 | 0.28 | 0.84 |
| 78 | 0.67 | 0.29 | 0.17 | 0.52 |
| 99 | 0.26 | 0.11 | 0.21 | 0.69 |
| 120 | 0.44 | 0.30 | 0.27 | 0.87 |
| 141 | 0.28 | 0.23 | 0.26 | 0.65 |
| 162 | 0.18 | 0.10 | 0.17 | 0.45 |
| 183 | 0.13 | 0.11 | 0.17 | 0.51 |
| 211 | 0.14 | 0.24 | 0.15 | 0.29 |
| 239 | 0.10 | 0.05 | 0.11 | 0.18 |
| 266 | 0.12 | 0.10 | 0.13 | 0.22 |
| 295 | 0.07 | 0.06 | 0.13 | 0.13 |
| 329 | 0.06 | | 0.06 | 0.13 |
| 365 | 0.14 | 0.06 | 0.16 | 0.09 |
| 380 | 0.14 | 0.06 | — | — |
| 395 | 0.17 | 0.08 | — | — |
| 429 | 0.20 | 0.06 | — | — |

Example 2

Dirofilariosis Infestation Test

For the tests, 7 adult dogs were divided into two groups: one group of 4 dogs have received an ivermectin implant as described in Example 1 and the second control group of 3 dogs (Dogs X, Y and Z) without any treatment.

These 7 dogs have been challenged at D365 (365 days after the implantation of the ivermectin implant by a subcutaneous injection of 2 mL of 75 *Dirofilaria immitis* L3 larvae).

The concentrations of ivermectin in the plasma, collected in the jugular vein, have been evaluated during 429 days for dogs A and 13 (Table 2, Example 1) or just dosed until D365 for dogs C and D.

*Dirofilaria immitis* infestations have been evaluated by serological tests done by Elisa detection test of *Dirofilaria immitis* (Canine Heartworm Antigen Test Kit, PetChek™ HTWM PF-Idexx) 150 days (D515), 195 clays (D560) or 240 clays (D605) after the D365 *dirofilaria* challenge.

The serological tests have been realized on dogs A to D at D560 and D605 after the implant were removed at D515. The 3 control dogs have been euthanasia at D515 to control definitively the serological data. The necropsy of the control dogs showed that half of the worms were in the lung artery, and half in the heart.

The infestation results are provided in the following Table 3.

TABLE 3

| | | Invermectine (ng/mL) | *Dirofilaria immitis* serological test | | |
|---|---|---|---|---|---|
| | | D365 | D515 | D560 | D605 |
| Implant | Dog A | 0.14 | Negative | Negative | Negative |
| | Dog B | 0.06 | Negative | Negative | Negative |
| | Dog C | 0.16 | Negative | Negative | Negative |
| | Dog D | 0.09 | Negative | Negative | Negative |
| Control | Dog X | — | Positive | — | — |
| | Dog Y | — | Positive | — | — |
| | Dog Z | — | Positive | — | — |

The invention claimed is:

1. A method of controlling heartworm disease in a dog, the method comprising administering to said dog an implant comprising ivermectin, wherein said implant maintains a concentration of ivermectin at about 0.10 ng per mL of plasma during a period of 6 months to 12 months after administering the implant, said concentration of ivermectin being effective to control *Dirofilaria immitis* or *Dirofilaria repens* infestation.

* * * * *